(12) United States Patent
Son (10) Patent No.: US 10,209,210 B2
(45) Date of Patent: Feb. 19, 2019

(54) MEASURING DEVICE USING ELECTRICAL CONDUCTIVITY AND HAVING FUNCTION OF INFORMING ELECTRODE CONTAMINATION

(71) Applicant: HM Digital Ltd., Seoul (KR)

(72) Inventor: Yun-Ho Son, Seoul (KR)

(73) Assignee: HM Digital Ltd., Seoul (KR)

( * ) Notice: Subject to any disclaimer, the term of this patent is extended or adjusted under 35 U.S.C. 154(b) by 41 days.

(21) Appl. No.: 15/293,072

(22) Filed: Oct. 13, 2016

(65) Prior Publication Data

US 2017/0108457 A1 Apr. 20, 2017

(30) Foreign Application Priority Data

Oct. 14, 2015 (KR) ........................ 10-2015-0143440

(51) Int. Cl.
| | | |
|---|---|---|
| *G01N 27/07* | (2006.01) | |
| *G01N 27/06* | (2006.01) | |
| *G01R 27/22* | (2006.01) | |
| *G01N 33/24* | (2006.01) | |
| *G01N 33/18* | (2006.01) | |

(52) U.S. Cl.
CPC ............ *G01N 27/07* (2013.01); *G01N 27/06* (2013.01); *G01N 33/1886* (2013.01); *G01N 33/24* (2013.01); *G01R 27/22* (2013.01)

(58) Field of Classification Search
CPC .... G01N 27/07; G01N 33/1886; G01N 27/06; G01N 33/24; G01R 27/22
USPC .................................. 324/691.693
See application file for complete search history.

(56) References Cited

U.S. PATENT DOCUMENTS

| | | | | |
|---|---|---|---|---|
| 7,619,423 B2 * | 11/2009 | Chen | ...................... | G01N 17/02 |
| | | | | 324/700 |
| 8,429,952 B1 * | 4/2013 | Bringhurst | ............ | A01N 59/16 |
| | | | | 73/53.01 |
| 2007/0018652 A1 | 1/2007 | Broadbent et al. | | |

FOREIGN PATENT DOCUMENTS

| | | |
|---|---|---|
| JP | 2002-005862 A | 1/2002 |
| JP | 2004-117085 A | 4/2004 |
| KR | 10-2010-0076400 | 7/2010 |

(Continued)

OTHER PUBLICATIONS

Korean Office Action dated Sep. 23, 2016 issued for Korean Patent Application No. 10-2015-0143440.

(Continued)

*Primary Examiner* — Amy He
(74) *Attorney, Agent, or Firm* — Kaplan Breyer Schwarz, LLP (57) ABSTRACT

The present invention relates to a measuring device using an electrical conductivity and having a function of informing electrode contamination. The measuring device includes a main body on which a display part is disposed on a surface thereof, and a control module controlling an operation of the measuring device is mounted therein, and a sensor unit disposed on one side of the main body and dipped into the object to measure electrical characteristics of the object to be measured. The sensor unit is driven by the control of the control module, and at least includes a first sensor electrode and a second sensor electrode for measuring electrical characteristics of the object to be measured. The sensor unit further includes a reference electrode disposed between the first and second electrodes at the same distance from each other.

12 Claims, 5 Drawing Sheets

(56) References Cited

FOREIGN PATENT DOCUMENTS

| KR | 101519356 | 5/2015 |
|----|-----------|--------|
| KR | 10-2015-0093980 | 8/2015 |

OTHER PUBLICATIONS

Japanese Office Action dated Jul. 18, 2017 issued for Japanese Patent Application No. 2016-202775.

\* cited by examiner

FIG. 1

PRIOR ART

FIG. 2

PRIOR ART

MEASURING DEVICE USING ELECTRICAL CONDUCTIVITY AND HAVING FUNCTION OF INFORMING ELECTRODE CONTAMINATION

CROSS-REFERENCE TO RELATED APPLICATIONS

This U.S. non-provisional patent application claims priority under 35 U.S.C. § 119 of Korean Patent Application No. 10-2015-0143440, filed on Oct. 14, 2015, the entire contents of which are hereby incorporated by reference.

BACKGROUND

The present invention relates to an electrical conductivity measuring device, and more particularly, to an electrical conductivity measuring device using the electrical conductivity and having an object to measure characteristics such as salinity or total dissolved solids (TDS), with being dipped into the object to be measured. Also, the present invention relates to the electrical conductivity measuring device having a function of informing electrode contamination, and for detecting whether or not an electrode is contaminated by the object to be measured and informing a user of the electrode contamination such that the electrode can be cleaned, thereby improving accuracy of a measured value.

In recent years, as awareness regarding the importance of management and usage of water resources increases, various management systems for pollution control and efficient usage of the water resources have been developed and applied. These water resources are managed to be used for various purposes such as drinking water or living water in an industrial site and a household.

In particular, as the general public is increasingly interested in well-being and health in recent years and also a salty food is revealed as a main factor for generating high blood pressure, interest in a salinometer measuring an amount of salt contained in a food is increasing. In general, the salinometer uses a property in which electrical conductivity is varied according to ion concentration of sodium chloride (NaCl) dissolved in the food. The salinometer calculates a salinity of corresponding measurement water such that a pair of electrodes contacts the measurement water, and then a voltage is applied to measure an amount of flowing current.

The above-described portable measuring device that is variously used for the household and the industrial site to measure characteristics of an object to be measure is being widely used. The portable measuring device may measure various characteristics by using electrical conductivity (EC) of an object to be measured and also accurately measure characteristics such as salinity, and total dissolved solids (TDS) according to the purpose thereof.

Figure 1:
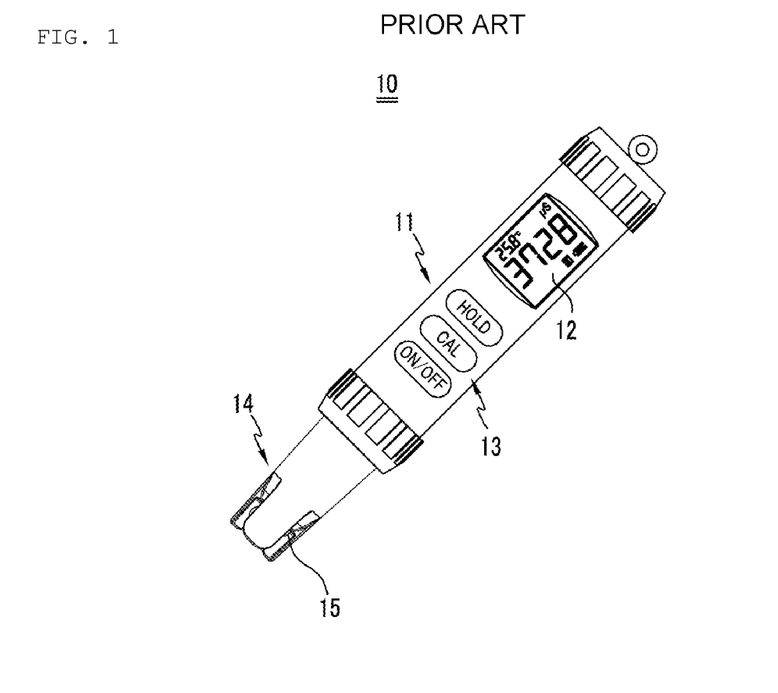
FIG. 1 is a perspective illustrating a portable salinometer according to a related art.
Figure 2:
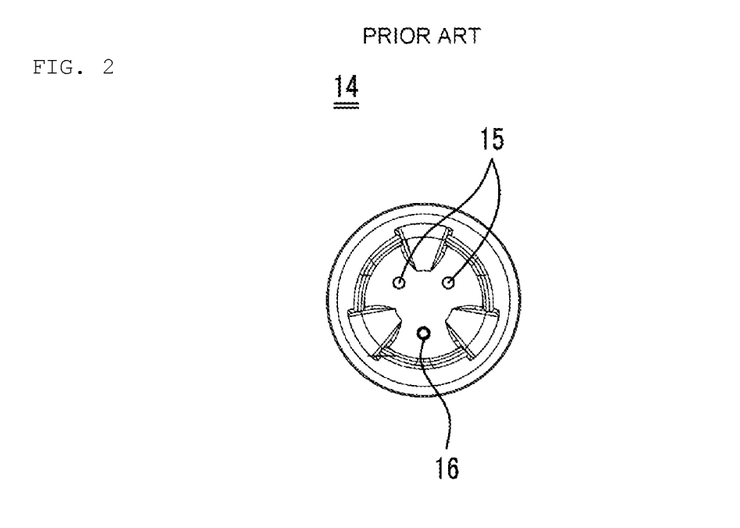
FIG. 2 is a front view illustrating a sensor unit that is a main part of FIG. 1.

FIG. 1 is a perspective view illustrating a portable salinometer according to a related art, and FIG. 2 is a front view illustrating a sensor unit that is a main part of FIG. 1.

First, as illustrated in FIG. 1, the portable salinometer includes a bar-shaped main body 11 having a predetermined length and a sensor unit 14 provided on one side end of the main body 11. A display panel 12 for displaying all sorts of information including a measured result and an operation part 13 for operating the measuring device are provided on the main body 11, and the sensor unit 14 includes a pair of salinity sensor electrodes 15 for being dipped into the object to be measured to measure the salinity and a temperature sensor electrode 16 for measuring temperature of the object to be measured.

Here, as illustrated in FIG. 2, the salinity sensor electrodes 15 are spaced apart by a predetermined distance from each other, and the salinity is measured on the basis of a resistance value measured such that a voltage is applied to both sensor electrodes 14 in a state in which the sensor unit 14 is sufficiently dipped into the measurement water. Here, the measured salinity is displayed as a salinity value in a state in which the temperature of the measurement water, which is measured by the temperature sensor electrode 16, is calibrated to an ordinary temperature.

According to the above-described related art, the salinometer automatically measures the salinity by using electrical characteristics, i.e., resistance values, measured between the pair of salinity sensor electrodes, to simply and rapidly measure the salinity of the measurement water. However, the above-described salinometer measuring the salinity by using the electrical characteristics between the pair of sensor electrodes has a problem in which the electrical characteristics between both sensor electrodes is significantly varied when a foreign substance is attached thereto to generate great error in the salinity measured on the basis of the measured electrical characteristics.

In general, since the salinometer needs to maintain cleanliness to perform the measurement, the electrodes need to be cleaned for every usage. In particular, when an object to be measured includes a food such as a soup or a stew, a material contained in the food may be easily attached to the sensor electrode, and fine foreign material may not be visually recognized to frequently generate errors in measurement of the salinity due to the contamination of the sensor electrode by the foreign substance. The above-described error in measurement may also occur when the electrical characteristic is varied due to degradation (such as a case in which a surface of the electrode is oxidized to generate rust) of the sensor electrode according to long period usage.

Thus, in the salinometer according to the related art, the sensor electrode is periodically calibrated by using a standard solution according to variation in the electrical characteristic due to the above-described contamination of the sensor electrode, and the sensor calibration device for this is disclosed in Korean Patent Registration No. 10-1519356 (prior art documents).

PRIOR ART DOCUMENTS

Patent Documents

Korean Patent Registration No. 10-1519356 (Registration date: May 6, 2015, "CALIBRATION DEVICE OF THE SENSOR")

SUMMARY OF INVENTION

To solve the above-described problem, the present invention provides a measuring device using an electrical conductivity and having a function of informing electrode contamination, and for detecting whether sensor electrodes is contaminated due to foreign substance attachment or oxidation and informing a user that the contamination occurs such that the user cleans the sensor electrodes, thereby improving accuracy of a measured value.

To accomplish the above-described purpose, an embodiment of the present invention provides a measuring device, which is dipped into the object to be measured, for measuring electrical characteristics of an object to be measured. The measuring device uses electrical conductivity and has a function of informing electrode contamination. The measuring device includes a main body on which a display part is disposed on a surface thereof, and a control module controlling an operation of the measuring device is mounted therein, and a sensor unit disposed on one side of the main body and dipped into the object to measure electrical characteristics of the object to be measured. The sensor unit is driven by the control of the control module, and at least includes a first sensor electrode and a second sensor electrode for measuring electrical characteristics of the object to be measured. The sensor unit further includes a reference electrode disposed between the first and second electrodes at the same distance from each other.

The control module controls the sensor unit to perform a measurement of the object to be measured when a difference between electrical characteristics of the first sensor electrode and the second sensor electrode, which are measured with respect to the reference electrode, is within an allowable reference value.

The control module controls the display unit to display cleaning information of the sensor electrode on the display part when the difference between electrical characteristics are deviated from the allowable reference value.

Here, when the electrical characteristics of the first sensor electrode and the second sensor electrode with respect to the reference electrode are different from each other or continuously and repeatedly deviated from the preset allowable reference value, the control module displays replacement information of the sensor electrode through the display part.

In an embodiment, the control module measures the electrical characteristics on the basis of a mean value with respect to the electrical characteristics of the first sensor electrode and the second sensor electrode, which are measured with respect to the reference electrode, or the control module measures the electrical characteristics of the first sensor electrode and the second sensor electrode to measure the electrical characteristics on the basis of the measured electrical characteristics.

DETAILED DESCRIPTION

The present invention and the technical objects achieved by the embodiment of the present invention will be clear by the exemplary embodiments that are described below. Exemplary embodiments of the present invention will be described below in more detail with reference to the accompanying drawings.

Figure 3:
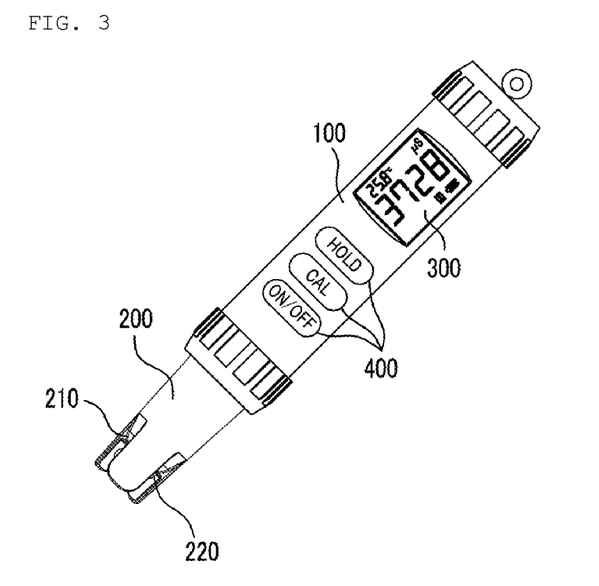
FIG. 3 is a perspective view illustrating a salinity measuring device according to an embodiment of the present invention.
Figure 4:
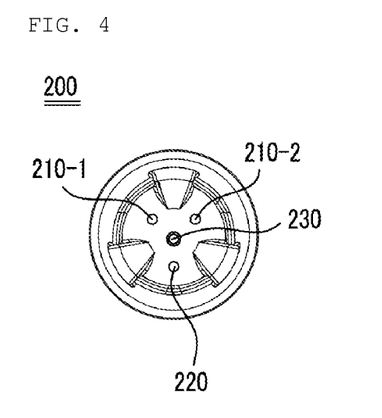
FIG. 4 is a front view illustrating a sensor unit that is a main part of FIG. 3.

FIG. 3 is a perspective view illustrating a salinity measuring device according to an embodiment of the present invention, and FIG. 4 is a front view illustrating a sensor unit that is a main part of FIG. 3.

As described above, the salinity measuring device includes a housing 100 and a sensor unit 200 provided on one side end of the housing 100. Here, a control module (refer to 100 in FIG. 5) controlling measurement of the sensor unit 200 and display of a display part 300 is embedded in the housing 100. Also, the display part 300 for displaying all sorts of information and an operation part 400 for receiving command of a user are provided on an outer circumferential surface of the housing 100.

Here, the housing 100 is a component for constituting a main body of the salinity measuring device and manufactured by injection molding using an insulating synthetic resin. The above-described housing 100 has a bar shape having a predetermined length so that the user may easily grab the device, and the display part 300 and the operation part 400 are provided on one side surface of the housing 100.

The sensor unit 200 is a component provided on one front end of the housing 100 to measure salinity of an object to be measured, i.e., measurement water and includes a pair of sensor electrodes 210 for measuring resistance of the measurement water and a temperature electrode 230 for measuring temperature of the measurement water. In particular, the salinity measuring device according to present invention further includes a reference electrode 220 for measuring resistance to the pair of sensor electrodes 210. That is, as illustrated in FIG. 4, a pair of sensor electrodes 210-1 and 210-2 each of which is an electrode for measuring resistance (i.e., electrical characteristic) of the measurement water and the reference electrode 220 are provided on the front end portion of the sensor unit 200 and exposed to the outside. The electrodes are spaced apart by a predetermined distance from each other. The above-described sensor electrode 210 and the reference electrode 220 are rod-shaped electrodes made of a metal material having excellent electrical conductivity.

Here, the pair of sensor electrodes 210 includes a first sensor electrode 210-1 and a second sensor electrode 210-2 to measure resistance between the first sensor electrode 210-1 and the second sensor electrode 210-2 by using a voltage applied to the sensor electrode 210 in a state in which the pair of sensor electrodes are dipped into the measurement water.

The reference electrode 220 is spaced apart form each of the pair of sensor electrodes 210 to measure the resistance between the reference electrode 220 and the first sensor electrode 210-1 or the second sensor electrode 210-2 to check whether the first sensor electrode 210-1 or the second sensor electrode 210-2 is contaminated or not. The reference sensor 220 is spaced apart by the same distance from the first sensor electrode 210-1 or the second sensor electrode 210-2. In a condition that the first sensor electrode 210-1 and the second sensor electrode 210-2 are not contaminated, the resistances between the reference electrode 220 and the first sensor electrode 210-1 and between the reference electrode 220 and the second sensor electrode 210-2 have the same value as each other. However, when a foreign substance is attached to any one side of the sensor electrodes, the resistance between the reference sensor 220 and the sensor electrode to which the foreign substance is attached has a value greater than that of the resistance between the reference sensor 220 and the sensor electrode to which the foreign substance is not attached.

Accordingly, the sensor unit 200 according to the present invention may detect which sensor electrode is contaminated and a degree of contamination on the basis of whether resistance values R1 and R2 between the reference sensor 220 and the first sensor electrode 210-1 and between the reference sensor 220 and the second sensor electrode 210-2 are the same as each other or whether at least difference therebetween is within an allowable reference value, and when the resistance values between the reference sensor 220 and the first sensor electrode 210-1 and between the reference sensor 220 and the second sensor electrode 210-2 are the same as each other or the difference therebetween is within the allowable reference value, all of the sensor electrodes are not contaminated or a contamination level is too low not to affect the measured result to thus perform the salinity measurement. On the other hand, when the difference of the resistance values between the reference sensor 220 and the first sensor electrode 210-1 and between the reference sensor 220 and the second sensor electrode 210-2 is deviated from the allowable reference value, since any one side or both sides of the sensor electrodes are contaminated to affect the measured value, the salinity measurement is not performed and the contamination state is notified through the display part 300, so that the user cleans the sensor unit 200 to re-use the device.

Here, in the salinity measurement, the salinity is calculated on the basis of a mean value ((R1+R2)/2) of the resistance values R1 and R2 of the first sensor electrode 210-1 and the second sensor electrode 210-2, which are measured with respect to the reference electrode 220 or the measured resistance values R1 and R2 of the first sensor electrode 210-1 and the second sensor electrode 210-2. For this, the control module may include a mean value calculating module. When the salinity is measured on the basis of the mean resistance value ((R1+R2)/2) of the first sensor electrode 210-1 and the second sensor electrode 210-2 with respect to the reference electrode 220, although any one sensor electrode is slightly contaminated, more exact salinity may be measured. When the salinity is measured on the basis of the resistance values R1 and R2 measured from the first sensor electrode 210-1 and the second sensor electrode 210-2, exact salinity value may be measured regardless of whether the reference electrode 220 is contaminated or not.

Also, the salinity measuring device according to the present invention may notice replacement time of the sensor electrode according to the difference of the resistance values of the first sensor electrode 210-1 or the second sensor electrode 210-2, which are measured with respect to the reference electrode 220. That is, the resistance values between the reference sensor 220 and the first sensor electrode 210-1 and between the reference sensor 220 and the second sensor electrode 210-2 are different to notice cleaning information through the display part 300, and when although the user tries the measurement again after cleaning, the resistance values are continuously and repeatedly different, since the sensor electrode itself is damaged due to oxidation or the like, the replacement information is noticed through the display part 300 to notice the replacement time of the sensor electrode to the user.

The temperature electrode 230 is an electrode for measuring actual temperature of the measurement water. Since the salinity is measured different according to the temperature of the measurement water, the actual temperature of the measurement water is necessary to be measured to calibrate the salinity measured in the measurement water having predetermined temperature to the salinity at ordinary temperature. Also, the temperature electrode 230 real-time measures temperature by a predetermined time unit from a moment in which the sensor unit 200 is dipped into the measurement water having high temperature.

The display part 300 may display various information such as a measuring mode, temperature, a measured value, a unit, a power of the measurement water and includes a LDC module. The above-described display part 300 is mounted on one side of the housing 100 to expose a display panel to the outside.

The operation part 400 is a component for user operation of the measuring device and has operation buttons having various functions such as an on/off button of the measuring device as needed.

The salinity measuring device having the above-described constitution performs the salinity measurement for the measurement water in a state in which the user grabs the housing 100 constituting the main body, and the sensor unit 200 is dipped into the measurement water so that each of the electrodes are sufficiently dipped into the measurement water. Also, the above-described measuring device may measure various characteristics regarding the measurement water according to the kinds of the sensor electrodes and be provided as the measuring device for measuring EC, TDS as well as the salinity.

Figure 5:
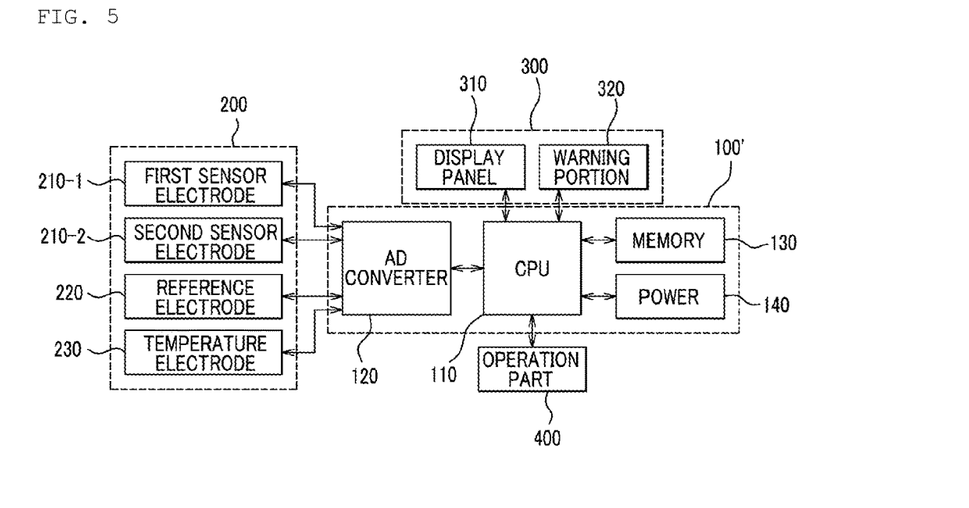
FIG. 5 is a block diagram illustrating an inner constitution of the salinity measuring device according to an embodiment of the present invention.
Figure 6:
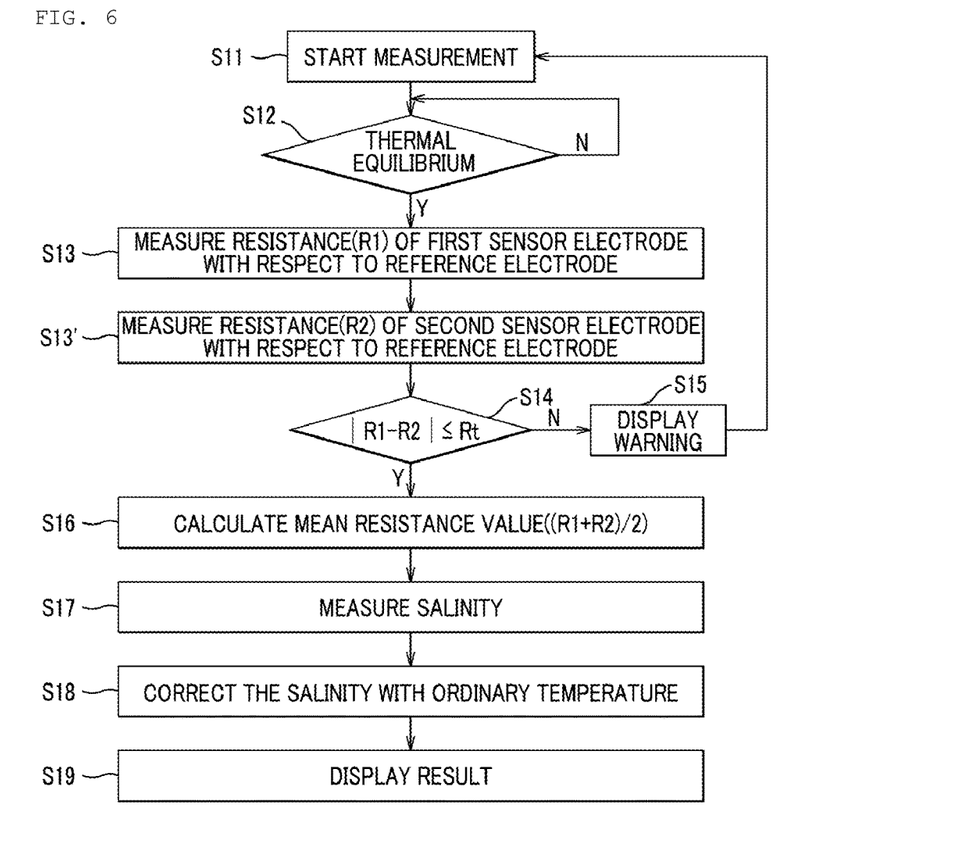
FIG. 6 is a flowchart illustrating a salinity measuring process of the salinity measuring device according to an embodiment of the present invention.

FIG. 5 is a block diagram illustrating an inner constitution of the salinity measuring device according to an embodiment of the present invention, and FIG. 6 is a flowchart illustrating a salinity measuring process of the salinity measuring device according to an embodiment of the present invention.

First, referring to FIG. 5, the salinity measuring device according to the present invention may perform the measurement according to the control of a control module 100' installed in the housing 100, and the control module 100' may include a main CPU 110, a AD converter 120, a memory 130, and a power 140, which may be integrated into a single microcomputer (MCU). An analog value such as current or temperature, which is detected from each of the electrodes of the sensor unit 200 is transmitted to the CPU 110 through the AD converter 120, and the CPU 110 provides the salinity value calculated on the basis of the transmitted value or a warning signal to the user through the display panel 310 or a warning portion 320 of the display part 300. Here, the display panel 310 displays various information including the salinity and temperature of the object to be measured, i.e., measurement water, and the warning portion 320 displays whether the sensor electrode 210 is contaminated or needed to be replaced. Here, the warning portion 320 may use a LED flasher to be provided separately from the display panel 310, and be disposed in the display panel 310.

Also, referring to the salinity measuring process using the salinity measuring device having the above-described constitution with reference to FIG. 6, in operation S11, when the sensor unit 200 is dipped into the measurement water, the measurement automatically begins, and in operation S12, whether the measurement water and each of the electrodes 210 and 220 are in a thermal equilibrium state (i.e., whether the temperature of the sensor electrode is equal to that of the measurement water) is checked according to the temperature measured by the temperature electrode 230 and an amount of variation in the measured temperature. When each of the electrodes and the measurement water are in the thermal equilibrium state, resistances R1 and R2 between the reference electrode and each of the sensor electrodes 210 are firstly measured. That is, in operations S13 and S13, the resistance R1 between the reference electrode 220 and the first sensor electrode 210-1 and the resistance R2 between the reference electrode and the second sensor electrode 210-2 are measured, and then in operation S14, the measured resistances R1 and R2 are compared with each other. When the resistances of the first sensor electrode 210-1 and the second sensor electrode 210-2 with respect to the reference electrode 220 are the same as each other or the difference therebetween is equal to or less than the reference value, the salinity measurement for the measurement water is performed. Here, in operation S16, the salinity measurement for the measurement water may calculate the mean value of the resistances R1 and R2 of the first sensor electrode 210-1 and the second sensor electrode 210-2 with respect to the reference electrode 220, and in operation S17, the salinity may be measured on the basis of the calculated mean value or the measured resistance values of the first sensor electrode 210-1 and the second sensor electrode 210-2.

Also, since the measured salinity is the salinity of the measurement water at predetermined temperature, in operations S18 and S19, the measured salinity is calibrated by the salinity in an ordinary temperature state as a final result to thus display the result through the display part 300.

On the other hand, when the resistances of the first sensor electrode 210-1 and the second sensor electrode 210-2 with respect to the reference electrode 220 in operations S12 and S12 are compared, and the comparative result is deviated from the reference value, since at least any one of the sensor electrodes 210 is contaminated by a foreign substance, information requiring cleaning is provided to the user through the display part 300 in operation S15, and when the sensor unit 200 is cleaned by the user, the same process is repeated to perform the measurement.

Also, when even after the sensor unit 200 is cleaned, the resistances between the reference electrode 220 and the first sensor electrode 210-1 and between the reference electrode 220 and the second sensor electrode 210-2 are compared and the comparative results are repeatedly and continuously different, since at least any one of the sensor electrodes 210 is damaged by oxidation or the like, information requiring replacement of the sensor electrode may be provided through the display part 300.

Also, in comparing the resistances between the reference electrode 220 and the first sensor electrode 210-1 and between the reference electrode 220 and the second sensor electrode 210-2, when the difference between both resistance values is equal to or less than the reference value although both resistance values are not completely the same as each other, the sensor electrodes are considered as a normal state, i.e., non-contaminated state, to measure the resistances of the first sensor electrode 210-1 and the second sensor electrode 210-2 to calculate the salinity.

Figure 7:
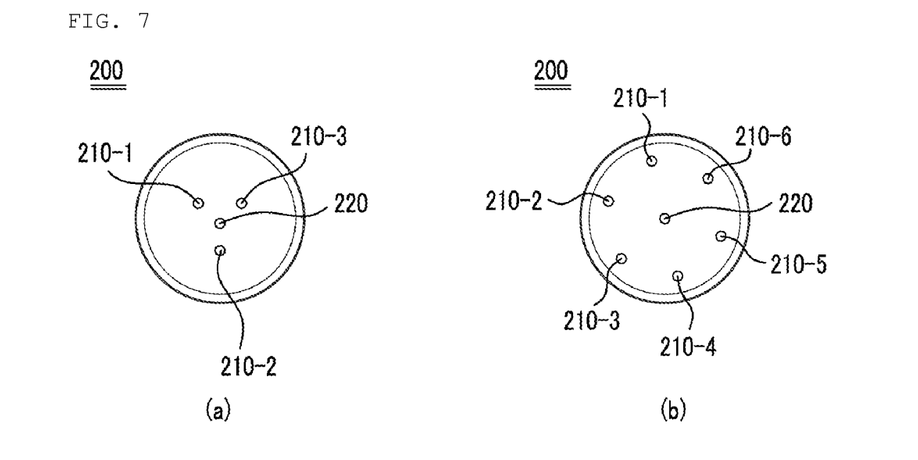
FIG. 7 a schematic conceptual view illustrating a sensor unit of a salinity measuring device according to another embodiment of the present invention.

FIG. 7 a schematic conceptual view illustrating the sensor unit of a salinity measuring device according to another embodiment of the present invention. The salinity measuring device according to another embodiment of the present invention includes the sensor unit 200 having a plurality of sensor electrodes 210 together with one reference electrode 220.

First, the sensor unit 200 illustrated in FIG. 7A includes three sensor electrodes 210-1, 210-2, and 210-3 with respect to one reference electrode 220. The reference electrode 220 and each of the sensor electrodes are spaced apart by the same distance, and the three sensor electrodes 210-1, 210-2, and 210-3 are also spaced apart by the same distance from each other. In this case, the resistances of the first sensor electrode 210-1, the second sensor electrode 210-2, and the third sensor electrode 210-3 with respect to the reference electrode 220 are measured, and then the salinity measurement for the measurement water is performed on the basis of the measured resistance value measured by a pair of sensor electrodes that have the same resistance value or the difference therebetween is small or within the reference value. For example, when the resistance values of the second sensor electrode 210-2 and the third sensor electrode 210-3 with respect to the reference electrode 220 are the same as each other, and the resistance value between the reference electrode 220 and the first sensor electrode 210-1 is greatly different, since the first sensor electrode 210-1 is contaminated, the salinity is measured on the basis of the mean value of the resistance values of the second sensor electrode 210-2 and the third sensor electrode 210-3 with respect to the reference electrode 220 or the measured resistance values of the second sensor electrode 210-2 and the third sensor electrode 210-3.

Also, as illustrated in FIG. 7B, six sensor electrodes 210-1 to 210-6 spaced apart by the same distance with respect to one reference electrode 220 are provided to measure the salinity on the basis of the mean value of the resistance values measured by at least two or more sensor electrodes each having the same resistance value or the difference therebetween is within the reference value range. As described above, as the number of the sensor electrode with respect to the reference electrode 220 increases, the salinity may be further exactly measured.

When at least three or more sensor electrodes are disposed as described above, although a portion of the sensor electrodes are contaminated, the pair of sensor electrodes that are not contaminated may perform the measurement to immediately perform the measurement without cleaning the contaminated sensor electrode. Here, when all of the sensor electrodes have the resistance values different from each other with respect to the reference electrode, cleaning information or replacement information is displayed to notice the information to the user.

Figure 8:
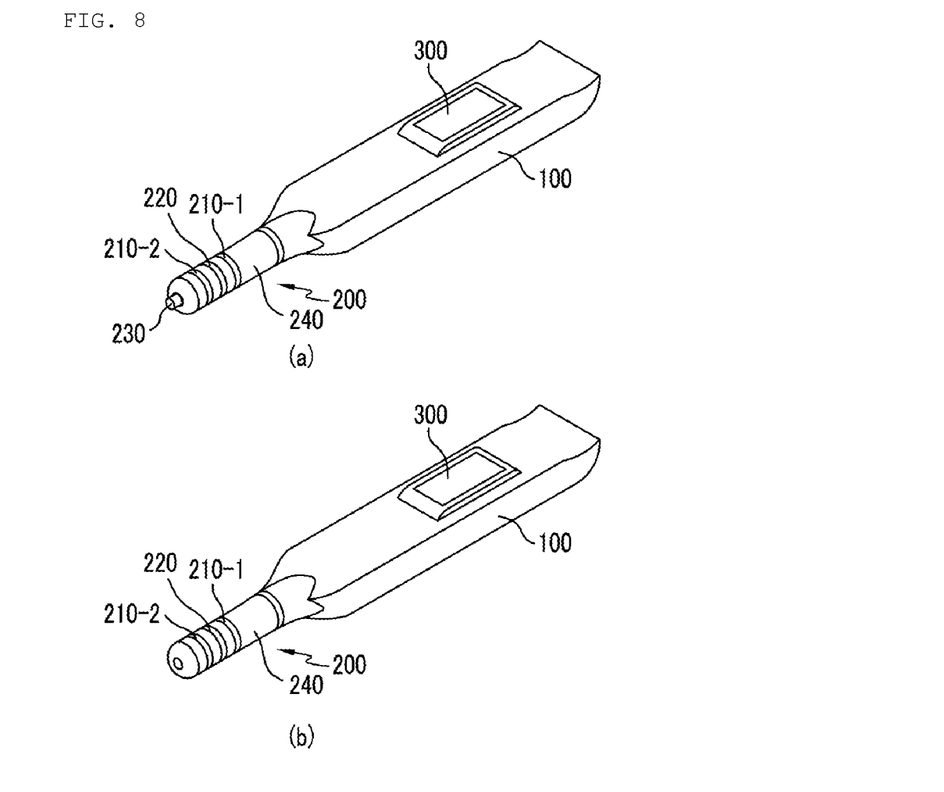
FIG. 8 is a perspective view illustrating a salinity measuring device according to another embodiment of the present invention.
Figure 9:
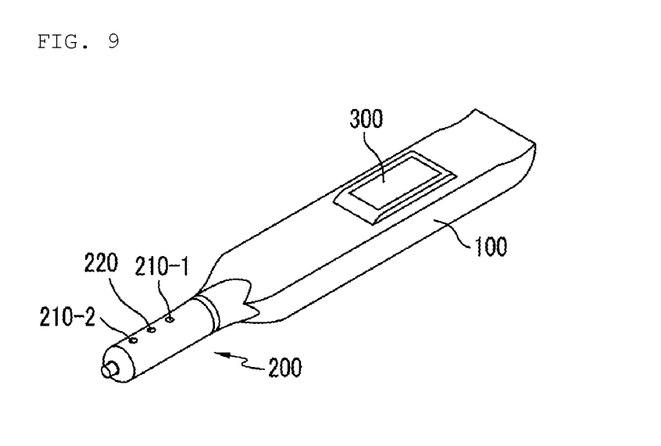
FIG. 9 is a perspective view illustrating a salinity measuring device according to another embodiment of the present invention.

FIGS. 8 and 9 are perspective views illustrating a salinity measuring device according to another embodiment of the present invention. The salinity measuring device according to another embodiment of the present invention has different electrode structure of the sensor unit.

First, referring to FIG. 8, the sensor unit 200 has a stripe structure in which the electrodes are arranged along a surface of a mold 240 made of an insulating material. That is, in the embodiment of FIG. 8, the reference electrode 220 and the sensor electrode 210 are stripe electrodes, and the central electrode is the reference electrode 220, and the first sensor electrode 210-1 and the second sensor electrode 210-2 are disposed on both sides of the reference electrode 220. Here, the first sensor electrode 210-1 and the second sensor electrode 210-2 are spaced apart by the same distance from the reference electrode 220. Here, the temperature electrode 230 may be disposed on an end of the mold 240 and exposed to the outside as in FIG. 8A or embedded in the mold 240 as in FIG. 8B.

Also, referring to FIG. 9, the sensor unit 200 has a spot structure on the surface of the mold 240 made of an insulating material. That is, in the embodiment of FIG. 9, the reference electrode 220 and the sensor electrode 210 are spot electrodes, and the central electrode is the reference electrode 220, and the first sensor electrode 210-1 and the second sensor electrode 210-2 are disposed on both sides of the reference electrode 220. Also, the temperature electrode is disposed on the end of the mold 240 and exposed to the outside or embedded in the mold 240.

Alternatively, the electrode of the sensor unit 200 may have a structure in which the stripe electrode and the spot electrode are mixed.

Also, according to an embodiment of the present invention, although the sensor unit 200 having the bar shape to be dipped into the measurement water (that is, the object to be measured) for the measurement is described, the sensor unit 200 may have a spoon shape in which a predetermined amount of the measurement water is accommodated in an accommodation groove to perform the measurement.

According to the present invention, as the reference electrode is further provided in addition to the pair of sensor electrodes, and the measurement is performed when the electrical characteristics of the pair of sensor electrodes with respect to the reference electrode are the same as each other or different within the reference value range, the measurement is performed to thereby measure the exact value.

Also, according to the present invention, when the sensor electrodes are contaminated or damaged, this information is provided to the user, so that the user may recognize the cleaning or replacement time of the sensor electrode to perform an appropriate action, thereby using the measuring apparatus conveniently.

Although the present invention is described with reference to the embodiments, a person having ordinary skill in the art will understand from the above that various modifications and other equivalent embodiments are also possible. In particular, although the salinity measuring device is described in explaining regarding the portable measuring device according to the present invention, the above-described constitution may be applied to the portable measuring device for measuring various characteristics such as the salinity and EC, or TDC of an object to be measured.

What is claimed is:

1. A measuring device, configured to be dipped into an object to be measured, for measuring electrical characteristics of the object to be measured, the measuring device using electrical conductivity and having a function of informing electrode contamination, the measuring device comprising:
   a main body on which a display part is disposed on a surface thereof, and a control module controlling an operation of the measuring device is mounted therein; and
   a sensor unit disposed on the main body and configured to be dipped into the object to measure electrical characteristics of the object to be measured, driven by the control of the control module, the sensor unit comprising:
      a plurality of electrodes at least including a first sensor electrode and a second sensor electrode configured to measure the electrical characteristics of the object to be measured, and
      a reference electrode disposed equidistant between each of the plurality of electrodes,
   wherein the control module controls the sensor unit to perform a measurement of the object to be measured when a difference between electrical characteristics of the first sensor electrode and the second sensor electrode, which are measured with respect to the reference electrode, is within an allowable reference value,
   wherein the control module controls the display unit to display cleaning information of the sensor electrode on the display part when the difference between the electrical characteristics are deviated from the allowable reference value.

2. The measuring device of claim 1, wherein, when the electrical characteristics of the first sensor electrode and the second sensor electrode with respect to the reference electrode are one of different from each other or continuously and repeatedly deviated from the preset allowable reference value, the control module displays replacement information of the sensor electrode through the display part.

3. The measuring device of claim 1, wherein the control module measures the electrical characteristics on the basis of a mean value with respect to the electrical characteristics of the first sensor electrode and the second sensor electrode, which are measured with respect to the reference electrode.

4. The measuring device of claim 1, wherein the control module measures the electrical characteristics of the first sensor electrode and the second sensor electrode.

5. The measuring device of claim 1, wherein the plurality of electrodes further comprises a plurality of pairs of electrodes,
   wherein the reference electrode being centrally disposed between each of the plurality of pairs of electrodes.

6. The measuring device of claim 1, wherein the plurality of electrodes further comprises a plurality of pairs of electrodes,
   wherein the reference electrode being disposed at equal distances between each of the plurality of pairs of electrodes.

7. The measuring device of claim 1, wherein each electrode of the plurality of electrodes further comprises a rod-shaped electrically conductive metal electrode.

8. The measuring device of claim 7, wherein the reference electrode further comprises a rod-shaped electrically conductive metal reference electrode.

9. The measuring device of claim 1, wherein each electrode of the plurality of electrodes further comprises an annular stripe electrode surrounded by an insulating material of the main body.

10. The measuring device of claim 9, wherein the reference electrode further comprises an annular stripe reference electrode surrounded by the insulating material of the main body,
   the reference electrode annular stripe being disposed at an equal distance between each annular stripe electrode of the plurality of electrodes.

11. The measuring device of claim 1, wherein each electrode of the plurality of electrodes further comprises a spot electrode surrounded by an insulating material of the main body.

12. The measuring device of claim 11, wherein the reference electrode further comprises a spot reference electrode surrounded by the insulating material of the main body,
   the reference electrode spot being disposed at an equal distance between each electrode spot of the plurality of electrodes.

* * * * *